United States Patent
Ancel et al.

(10) Patent No.: US 7,323,574 B2
(45) Date of Patent: Jan. 29, 2008

(54) PROCESS FOR THE PREPARATION OF PHENYL PYRAZOLE COMPOUNDS

(75) Inventors: Jean-Erick Ancel, Saint Genis Laval (FR); Joelle Vidal, Rennes (FR)

(73) Assignee: BASF Agro B.V. Arnhem, (NL) -- Wadenswil Branch (CH)

( * ) Notice: Subject to any disclaimer, the term of this patent is extended or adjusted under 35 U.S.C. 154(b) by 0 days.

(21) Appl. No.: 11/529,051

(22) Filed: Sep. 28, 2006

(65) Prior Publication Data
US 2007/0021620 A1    Jan. 25, 2007

Related U.S. Application Data

(62) Division of application No. 10/519,823, filed as application No. PCT/EP03/08212 on Jun. 30, 2003, now Pat. No. 7,129,372.

(30) Foreign Application Priority Data
Jul. 5, 2002    (EP)    ................... 02356131

(51) Int. Cl.
*C07D 231/10*    (2006.01)
*C07D 255/32*    (2006.01)

(52) U.S. Cl. ............... 548/367.4; 548/356.1; 548/366.1; 558/303; 558/388; 558/394; 558/436

(58) Field of Classification Search ............ 548/356.1, 548/366.1, 367.4; 558/303, 388, 389, 390, 558/394, 436
See application file for complete search history.

(56) References Cited

U.S. PATENT DOCUMENTS 7,129,372 B2 * 10/2006 Ancel et al. ............... 558/436

FOREIGN PATENT DOCUMENTS

| EP | 0234119 | 12/1988 |
|----|---------|---------|
| EP | 0295117 | 12/1988 |
| EP | 0966445 | 7/2001  |

OTHER PUBLICATIONS

Beeler, A.B. et al., "Synthesis of fipronil sulphide, an active metabolile, from the parent insecticide Flpronil", Tetrahedron Letters, vol. 42, No. 32, Aug. 6, 2001, pp. 5371-5372, Search Report.

Kopranenkov, V.N. et al., "Phthaloyanines and related compounds, XVI. Synthesis and Electronic Absorption Spectra of amino-alkoxy-, and alkylthio-substituted porphyrazines" Journal of General Chemistry of the USSR, vol. 15, No. 4, Pt. Apr. 1, 1979, pp. 962-967, Search Report.

Hainzl, D. et al. "Mechanisms for selective toxicity of fipronil insecticide and its sulphone metabolite and desulphinyl photoproduct", Chemical Research in toxicology, vol. 11, No. 12., Nov. 7, 1998, pp. 1529-1535, Search Report.

Turpin, A. et al., "Préparation et étude en effet Faraday de quelques esters el du dinitrile de l'aclde acétylene-dicarboxylique ainsi que leurs composés d'addition avec les thiols" Comptes Rendus Hebdomadaires Des Seances De l'Academie des Sciences, vol. 256, 1963, pp. 1712-1714, Search Report.

Leivers et al., "A forbidden Rearrangement", Organic Letters, vol. 5, No. 19, 2003, pp. 3407-3409.

Andre et al. "Preparation and study of the Faraday effect of several esters and the dinitrile of acetylenecarboxylic acid as well as their addition compounds with thilos", Compt. Rend, 1963, 256, pp. 1712-1714 (CAS Abstract Only).

* cited by examiner

*Primary Examiner*—Golam M. M. Shameem
(74) *Attorney, Agent, or Firm*—Hutchison Law Group PLLC

(57) ABSTRACT

A process for the preparation of compound (III) which comprises the reaction between a compound of general formula (V) and dicyano acetylene (IV), said reaction carried out in the presence of water

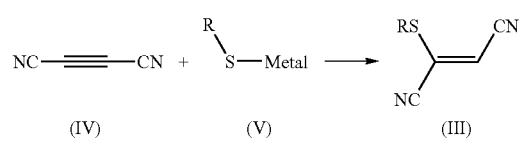

wherein R is selected from $CF_3$, or $C_1$ to $C_6$ alkyl
M is an alkaline or alkaline-earth metal or silver.

13 Claims, No Drawings

PROCESS FOR THE PREPARATION OF PHENYL PYRAZOLE COMPOUNDS

This application is a divisional of U.S. application Ser. No. 10/519,823, filed Jul. 13, 2005, now U.S. Pat. No. 7,129,372, incorporated herein by reference in its entirety, which is the National Stage of International Application No. PCT/EP2003/008212, filed Jun. 30, 2003, which International Application claims priority to European Patent Application No. 02356131.9, filed Jul. 5, 2002.

The present invention relates to a process for preparing pesticidal intermediates, and to novel 2-arylhydrazono succinonitrile compounds and to 2-arylhydrazino succinonitrile compounds.

European Patent Publication Nos. 0295117 and 0234119 describe the pesticidally active phenylpyrazole compounds and of 5-amino-1-aryl-3-cyanopyrazole intermediate compounds used in their synthesis. Various methods for preparing these compounds are known, in particular through various intermediate compounds. European Patent No. 0966445 discloses a process for the preparation of a pyrazole compound, formula (II) which is then used to prepare a trifluoromethyl sulfinyl derivative, generally known as fipronil. The process is as shown in the reaction scheme below, starting from an aryl-hydrazine, formula (I):

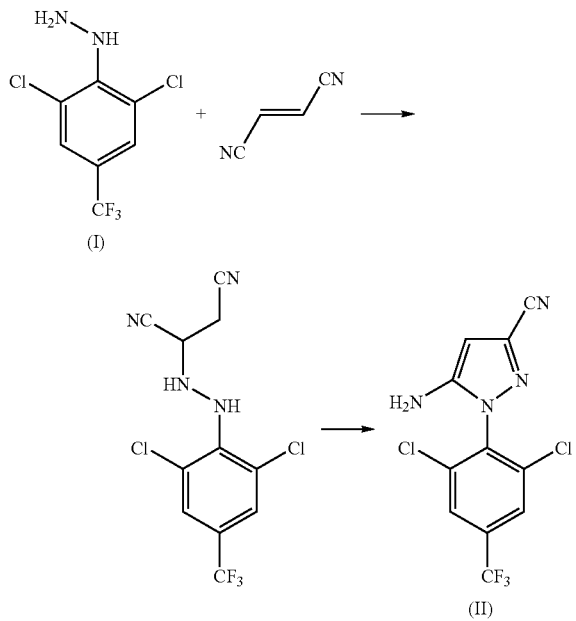

Unfortunately, this process does not give a direct access to fipronil derivatives, and still requires a further sulphenylation step.

We have now found a method that gives a direct access to sulphenylated derivatives of pyrazole (II).

Accordingly, the present invention provides a process for the preparation of compound (III) which comprises the reaction between a compound of general formula (V) and dicyano acetylene of formula (IV), said reaction carried out in the presence of water

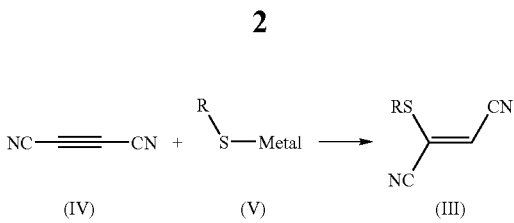

wherein R is selected from $CF_3$, or $C_1$ to $C_6$ alkyl; and
M is silver or an alkaline or alkaline-earth metal The preferred compound of formula (V) is when R is trifluoro methyl ($CF_3$) and M is silver.

The process of the present invention may be carried out in the presence of a solvent The solvent is preferably an organic solvent that is miscible with water. Suitable solvents include acetone and tetrahydrofuran.

The process may be carried out at a temperature of from −100 to +50° C., preferably from −80 to +20° C. Concentration of the reactants may be from 0.01 to 5 moles per liter of solvent.

The molar ratio of dicyano acetylene to compound of formula (V) is from 5:1 to 1:5. the preferred molar ratio is 1:1.

When R of compound (V) is CF3, the resulting compound III is a novel compound and thus according to another aspect of the present invention, there is provided a novel compound (III) wherein R is $CF_3$ Compound of formula (III) may be used to prepare a known and key intermediate compound of fipronil and according to a further aspect of the present invention there is provided a process for the preparation of compound (VII) which comprises a first step of reaction of an aryl hydrazine of compound (I) with a compound of general formula (III) to produce an intermediate compound of general formula (VI); and a second step which comprises the oxidation of compound (VI),

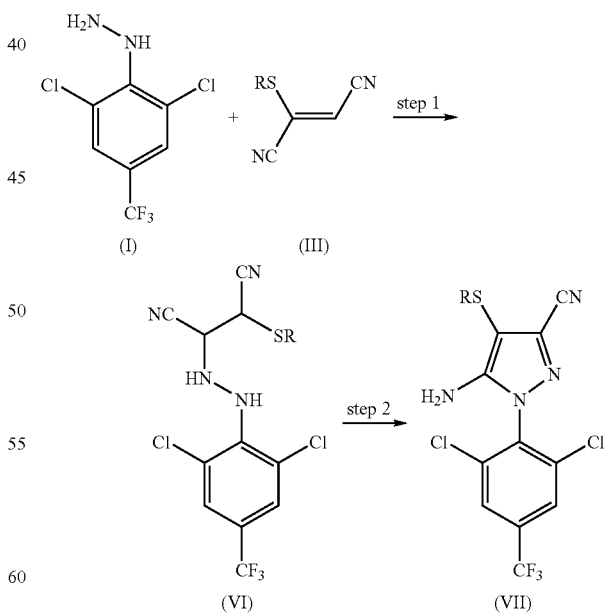

wherein R is selected from $CF_3$, or $C_1$ to $C_6$ alkyl;

Compound of formula (III) is as defined above and may be used in the form of the cis-isomer maleonitrile or the trans isomer fumaronitrile. Optionally a mixture of both isomers may be used. Arylhydrazines of formula (I) are known or may be prepared by known methods.

The preferred compounds of formula (VI) have the same values of R as for compounds of formula (III). Most preferably, compound of formula (VI) is 1-trifluoromethyl thio 2-(2,6-dichloro-4-trifluoromethyl phenylhydrazino) succinonitrile.

The first step of the process may be carreid out in the presence of a solvent. Suitabke solvents include polar solvents such as tetrahydrofurane, N-methylpyrrolidone, N,N-dimethylformamide or dimethylsulphoxide. The reaction may alternatively be carried out in the absence of a solvent by heating a mixture of the two reactants, namely compounds of formula (III) and (I).

The first step of the process may also be carried out in the presence of a catalyst such as a tetra-alkylammonium salt for example N-benzyltrimethylammonium hydroxide, or alanine.

The reaction temperature in the first step of the process may be from 0 to 150° C., preferably from 20 to 100° C.

The reaction may be carried out using a molar ratio of a compound of formula (III) to a compound of formula (I) of from 1:10 to 10:1, preferably from 1:1 to 5:1, especially from 1.1 to 1.

When R of compound (VI) is CF3, the resulting compound (VI) is a novel compound and thus according to another aspect of the present invention, there is provided a novel compound (VI) wherein R is $CF_3$ Compounds of formula (VI) may be obtained as a mixture of syn and anti isomers and all such forms are embraced by the present invention.

The second step of the process comprises the oxidation of ompound of formula (VI) to provide a hydrazone compound. Suitable oxidants for use in the second step include quinones such as benzoquinone, peroxides such as hydrogen peroxide, hypohalites such as sodium hypochlorite, or an alkali metal hydroxide such as sodium hydroxide in the presence of air or preferably a metal salt or oxide, for example, cupric chloride or mercuric oxide.

The oxidation reaction may be carried out in the presence of a solvent. Solvents suitable include aromatic halogenated or non-halogenated hydrocarbons such as toluene or chlorobenzene, nitriles such as acetonitrile or amides such as N,N-dimethylformamide.

The oxidation step may be carried out at a temperature of from 20 to 150° C., preferably from 50 to 100° C.

The aforementioned oxidation reaction may be merged with a spontaneous cyclisation of the intermediate hydrazone to produce the corresponding Pyrazole

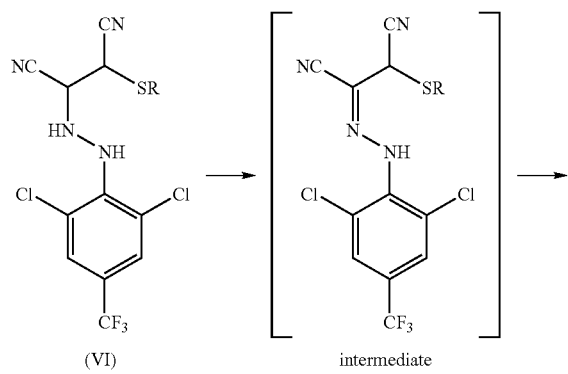

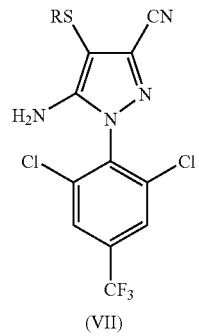

The present invention will now be illustrated with reference to the following examples:

EXAMPLE 1

Preparation of 5-amino-3-cyano-1-(2,6-dichloro-4-trifluoro methyl-phenyl) pyrazole Hydrazine (290 miligrams, 1.2 mmol) was added to a solution of dicyano acetylene (84 mg, 1.1 mmol) in chloroform (2 ml). The mixture was stirred for 30 minutes at ambient temperature then heated to 50° C. for 3 hours. Purification by flash chromatography on silica gel and crystallisation from dichloromethane/hexane provided a white solid (316 mg; 89%) which was recrystallised in a mixture of hexane/toluene (ratio 2/1) to give the title compound (288 mg, 81% yield).

EXAMPLE 2

Preparation of 1,2-Dicyano-1-(trifluoromethylthio)ethene

A solution of $CF_3SAg$ (836 mg; 4 mmol) in 2 ml of acetone chilled to -78° C. under argon was added to dicyanoacetylene (305 mg; 4 mmol) and water(85 mg) in 4 ml of acetone. The resulting mixture was shaken for 12 hours. The mixture was allowed to reach 20° C. Purification by flash chromatography on silica gel and crystallization from dichloromethane/hexane provided a mixture of the two isomers of the title compound (275 mg, 39% yield) in the form of a brown oil.

EXAMPLE 3

Preparation of 1-(2,6-dichloro-4-trifluoromethylphenylhydrazono) 1,2-dicyano-2-trifluoromethylthio ethane A mixture of 1,2-Dicyano-1-(trifluoromethylthio)ethene (275 mg;1.5 mmol), obtained in Example 2, hydrazine (378 mg; 1.5 mmol) and 6 ml of tetrahydrofuran was stirred at ambient temperature for 24 hours. Purification by flash chromatography on silica gel and crystallisation from dichloromethane/hexane gave. a light brown solid of the title product (442 mg, 67% yield) in a 60/40 mix of the two isomers. The main isomer was dissolved in chloroform and isolated after suspending in 5 ml of CHCL3, filtering and washing (80 mg, 12% yield).

EXAMPLE 4

Preparation of 5-amino-3-cyano-1-(2,6-dichloro-4-trifluoro methyl-phenyl)-4-trifluoromethylthio pyrazole A mixture of 1-(2,6-dichloro-4-trifluoromethylphenylhydrazono) 1,2-dicyano-2-trifluoromethylthio ethane (144 mg; 0.34 mmol), prepared according to Example 3, copper (II) chloride (97 mg; 0.71 mmol), and 4 ml of chlorobezene was stirred for 4 hours at 100° C. The solvent was then evaporated under vacuum. The residue was dissolved in CH2CL2 and the solution was washed by an aqueous solution of 1% ammonia in water. The product was dried over sodium sulphate, and solvent was evaporated under reduced pressure. Purification by flash chromatography on silica gel and crystallization from dichloromethane/hexane gave a white solid (105 mg; 73% yield). The product was then recrystallized in a hexane/toluene mixture to provide a light brown powder (93 mg; 65% yield), melting point 163° C. A second recrystallization provided a white powder of the title product with a melting point 165° C.

What is claimed is:

1. Novel compound according to general formula (III)

(III)

wherein R is $CF_3$.

2. A process for the preparation of compound (VII) which comprises a first step of reaction of an aryl hydrazine of compound (I) with a compound of general formula (III) to produce an intermediate compound of general formula (VI), and a second step which comprises the oxidation of the compound (VI), according to the reaction scheme below

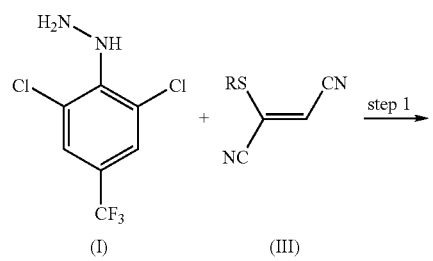

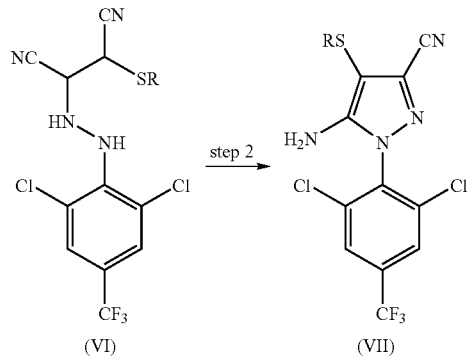

where R is selected from $CF_3$ or $C_1$ to $C_6$ alkyl.

3. A process as claimed in claim 2 wherein the compound of formula (VI) is 1-trifluoromethyl thio 2-(2,6-dichloro-4-trifluoromethyl phenylhydrazino) succinonitrile.

4. A process as claimed in claim 2 carried out in the presence of a polar solvent selected from tetrahydrofuran N-methylpyrrolidone, N,N-dimethylformamide and dimethylsulphoxide.

5. A process as claimed in claim 2 carried out in the presence of a catalyst selected from N-benzyltrimethylammonium hydroxide, or alanine.

6. A process as claimed in claim 2 carried out at a temperature of from 0 to about 150° C.

7. A process as claimed in claim 2 wherein the molar ratio of the compound of formula (III) to the compound of formula (I) is from 1:10 to 10:1.

8. A process as claimed in claim 2 wherein the second step is carried out in the presence of a quinone, a peroxide, a hypohalite or an alkali metal hydroxide.

9. A process as claimed in claim 2 wherein the second step is carried out in the presence of air and optionally a metal salt or oxide.

10. A process as claimed in claim 2 wherein the second step is carried out in the presence of an aromatic halogenated or non-halogenated hydrocarbon solvent.

11. A process as claimed in claim 2 wherein the second step is carried out at a temperature of from 20 to 150° C.

12. Novel compound according to general formula (VI)

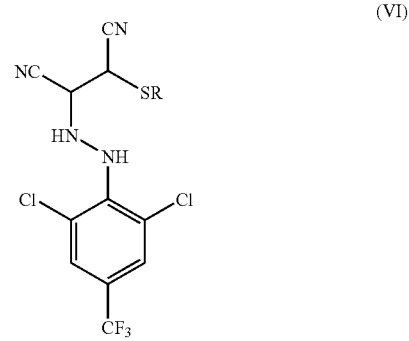

(VI)

wherein R is $CF_3$.

13. A process as claimed in claim 3 carried out in the presence of a polar solvent selected from tetrahydrofuran, N-methylpyrrolidone, N,N-dimethylformamide and dimethylsulphoxide.

* * * * *